(12) United States Patent
Tirtowidjojo et al.

(10) Patent No.: US 8,664,453 B2
(45) Date of Patent: Mar. 4, 2014

(54) MULTI-STAGE PROCESS AND APPARATUS FOR RECOVERING DICHLOROHYDRINS

(75) Inventors: Danil Tirtowidjojo, Lake Jackson, TX (US); Andrei S. Merenov, Lake Jackson, TX (US); Christian D. Kneupper, Brazoria, TX (US); Bruce D. Hook, Lake Jackson, TX (US); Anil I. Mehta, Lake Jackson, TX (US)

(73) Assignee: Dow Global Technologies Inc., Midland, MI (US)

( * ) Notice: Subject to any disclaimer, the term of this patent is extended or adjusted under 35 U.S.C. 154(b) by 770 days.

(21) Appl. No.: 12/595,480

(22) PCT Filed: Apr. 11, 2008

(86) PCT No.: PCT/US2008/059968
§ 371 (c)(1),
(2), (4) Date: Oct. 9, 2009

(87) PCT Pub. No.: WO2008/128004
PCT Pub. Date: Oct. 23, 2008

(65) Prior Publication Data
US 2010/0137652 A1 Jun. 3, 2010

Related U.S. Application Data

(60) Provisional application No. 60/923,108, filed on Apr. 12, 2007.

(51) Int. Cl.
*C07C 29/82* (2006.01)
(52) U.S. Cl.
CPC ..................................... *C07C 29/82* (2013.01)
USPC ........................................................ 568/844
(58) Field of Classification Search
CPC ....................................................... C07C 29/82
USPC ........................................................ 568/844
See application file for complete search history.

(56) References Cited

U.S. PATENT DOCUMENTS 4,634,784 A   1/1987   Nagato et al.

FOREIGN PATENT DOCUMENTS

| CN | 10107751 | 8/2007 | |
|---|---|---|---|
| DE | 197308 | 11/1906 | |
| EP | 1752435 | 2/2007 | |
| EP | 1762556 | 3/2007 | |
| EP | 1762556 A1 * | 3/2007 | .............. C07C 29/62 |
| WO | 2005021476 | 3/2005 | |
| WO | WO 2005054167 A1 * | 6/2005 | |
| WO | 2006020234 | 2/2006 | |
| WO | 2008128004 | 11/2008 | |

OTHER PUBLICATIONS

Kirk-Othmer Encyclopedia of Chemical Technology, 5th Edition (John Wiley and Sons, 2004) vol. 13, pp. 825-827.

* cited by examiner

*Primary Examiner* — Joseph Kosack
*Assistant Examiner* — Matthew Coughlin

(57) ABSTRACT

A process and apparatus for recovering dichlorohydrins from a mixture comprising dichlorohydrins, one or more compounds selected from esters of dichlorohydrins, monochlorohydrins and/or esters thereof, and multihydroxylated-aliphatic hydrocarbon compounds and/or esters thereof, and optionally one or more substances comprising water, chlorinating agents, catalysts and/or esters of catalysts is disclosed. The mixture is distilled or fractionated to separate a lower boiling fraction comprising dichlorohydrin(s) from the mixture to form a higher boiling fraction comprising the residue of the distillation or fractionation. The higher boiling fraction is stripped to recover remaining dichlorohydrins. Advantages include more efficient recovery of dichlorohydrins for a given distillation column, less waste due to avoiding the conditions conducive to the formation of heavy byproducts, and reduced capital investment in recovery equipment.

11 Claims, 1 Drawing Sheet

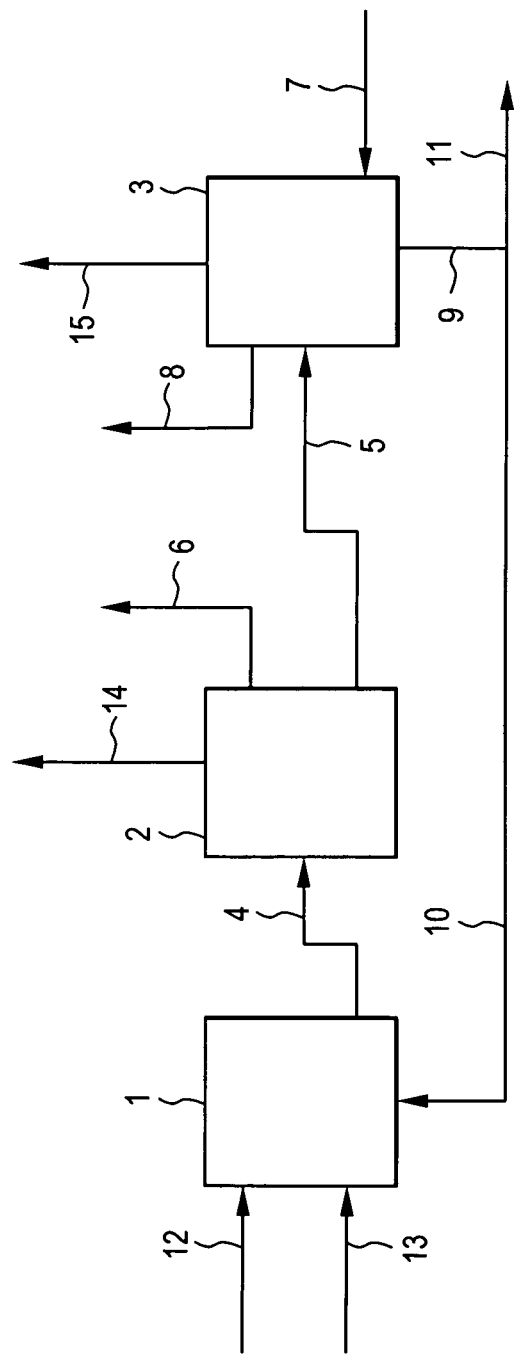

MULTI-STAGE PROCESS AND APPARATUS FOR RECOVERING DICHLOROHYDRINS

CROSS REFERENCE TO RELATED APPLICATIONS

This is a §371 application of PCT International Patent Application Number PCT/US2008/059968 filed Apr. 11, 2008, and claims priority from provisional application Ser. No. 60/923,108 filed Apr. 12, 2007, each of which is incorporated herein by reference in its entirety.

BACKGROUND OF THE INVENTION

The present invention relates to processes and apparatus for recovering dichlorohydrins from a mixture comprising the same such as the effluent generated by a process for converting multihydroxylated-aliphatic hydrocarbon compound(s) and/or ester(s) thereof to chlorohydrins.

Dichlorohydrins are useful in preparing epoxides such as epichlorohydrins. Epichlorohydrin is a widely used precursor to epoxy resins. Epichlorohydrin is a monomer which is commonly used for the alkylation of para-bisphenol A. The resultant diepoxide, either as a free monomer or oligomeric diepoxide, may be advanced to high molecular weight resins which are used for example in electrical laminates, can coatings, automotive topcoats and clearcoats.

Glycerin is considered to be a low-cost, renewable feedstock that is a co-product of the biodiesel process for making fuel. It is known that other renewable feedstocks such as fructose, glucose and sorbitol can be hydrogenolized to produce mixtures of vicinal diols and triols, such as glycerin, ethylene glycol, 1,2-propylene glycol, 1,3-propylene glycol and the like. With abundant and low cost glycerin or mixed glycols, economically attractive processes for recovering dichlorohydrins from effluents produced by the above processes are desired.

A process is known for the conversion of glycerol (also referred to herein as "glycerin") to mixtures of dichloropropanols, compounds I and II, as shown in Scheme 1 below. The reaction is carried out in the presence of anhydrous HCl and an acetic acid (HOAc) catalyst with water removal. Compounds I and II can then be converted to epichlorohydrin via treatment with caustic or lime.

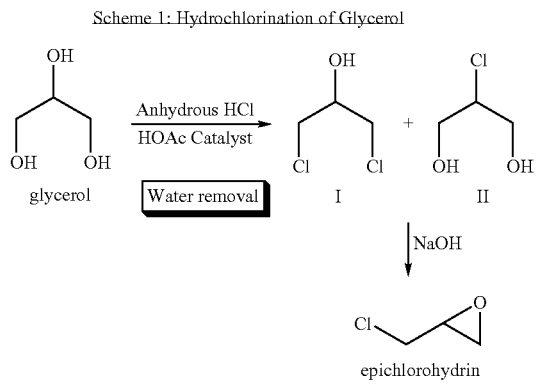

Various processes using the above chemistry in Scheme 1 have been reported in the prior art. For example, epichlorohydrin can be prepared by reacting a dichloropropanol such as 2,3-dichloro-1-propanol or 1,3-dichloro-2-propanol with base. Dichloropropanol, in turn, can be prepared at atmospheric pressure from glycerol, anhydrous hydrochloric acid, and an acid catalyst. A large excess of hydrogen chloride (HCl) was recommended to promote the azeotropic removal of water that is formed during the course of the reaction.

WO 2006/020234 A1 describes a process for conversion of a glycerol or an ester or a mixture thereof to a chlorohydrin, comprising the step of contacting a multihydroxylated-aliphatic hydrocarbon compound, an ester of a multihydroxylated-aliphatic hydrocarbon, or a mixture thereof with a source of a superatmospheric partial pressure of hydrogen chloride to produce chlorohydrins, esters of chlorohydrins, or mixtures thereof in the presence of an organic acid catalyst. This process is also referred to herein as a "dry process". Azeotropic removal of water in a dry process via a large excess of hydrogen chloride is not required to obtain high chlorohydrins yield. Separation of the product stream from the reaction mixture may be carried out with a suitable separation vessel such as one or more distillation columns, flash vessels, extraction columns or adsorption columns. WO 2006/020234 A1 does not describe a specific distillation method or a method to minimize formation of heavy byproducts.

WO 2005/021476 A1 describes a process using atmospheric partial pressure of hydrogen chloride, acetic acid as the catalyst, and a cascade of loops, preferably three loops, each loop consisting of a reactor and a distillation column in which water of reaction, residual hydrogen chloride and dichloropropanol are removed from the reaction effluent. This process for distillation requiring a cascade of reactor/distillation loops is very expensive as it requires several reactors/columns in the process. WO 2005/021476 A1 also does not describe a specific distillation method or a method to minimize formation of heavy byproducts. Furthermore, valuable acetic acid is lost with the distillate, needing to add more acetic acid to make up for the catalyst loss in distillation.

EP 1 752 435 A1 discloses another process for producing a chlorohydrin by reaction between a multihydroxylated aliphatic hydrocarbon and/or an ester thereof and aqueous hydrogen chloride to produce chlorohydrins, esters of chlorohydrins, or mixtures thereof under atmospheric condition in which a purge from the reactor bottom is fed to a stripper in which partial stripping of most of unreacted hydrogen chloride, the water from the aqueous hydrogen chloride reactant and water that is formed during the course of the reaction (also referred to herein as "water of reaction"), from the reaction mixture is carried out and a distillation or stripping column is fed with the liquid phase from the stripper. The gas phase from the stripper, which contains most of the unreacted hydrogen chloride, the excess water from the aqueous hydrogen chloride reactant and the reaction by-product water from the reaction mixture, is conducted to a distillation column fed by the vapor produced by the reactor or is recycled directly to the reactor. The main fraction of dichloropropanol is collected from the top of the distillation or stripping column. The column residue is recycled to reactor. This process (also referred to herein as a "wet process"), not only adds water via the aqueous hydrogen chloride reactant into the process, but also produces water of reaction in the process. The removal of large excess of water in the wet process via stripper is less energy efficient and unnecessary for the dry process. A better utilization of the stripper can be done in the recovery of dichloropropanol. EP 1 752 435 A1 also does not describe specific distillation method to minimize formation of heavy byproducts.

CN 101007751A describes another process that combines wet and dry processes with two reactor in series, in which tubular reactor is used as the first reactor and foaming-tank reactor is used as the second reactor. Aqueous hydrogen chloride, glycerin, carboxylic acid catalyst are mixed and fed to the first reactor and gaseous hydrogen chloride is fed to the second reactor. Inert impurities are added to the gaseous hydrogen chloride feed in order to improve the efficiency of stripping water from the reaction mixture in the foaming-tank reactor. The azeotropic composition of generated water, dichloropropanol and hydrogen chloride and part of the catalyst are evaporated from the top of foaming-tank reactor. The liquid bottom product of the foaming-tank reactor enters to a rectifying tower for separation. The dichloropropanol product is obtained from the rectifying tower distillates and the tower bottom residue is recycled to the foaming-tank reactor. This process shows lower hydrogen chloride conversion than that of the dry process, generates excess water where azeotropic removal of water is required, which implies larger process equipment than that of the dry process. CN 101007751A also does not describe a specific distillation method to minimize formation of heavy byproducts.

Opportunities remain to further improve the recovery of dichlorohydrins in a form that can be used in subsequent conversions, such as the conversion to epichlorohydrin.

SUMMARY OF THE INVENTION

One aspect of the present invention is a process for recovering dichlorohydrin(s) from a mixture comprising dichlorohydrin(s), one or more compounds selected from ester(s) of chlorohydrin(s), monochlorohydrin(s), and/or multihydroxylated-aliphatic hydrocarbon compound(s) and/or ester(s) thereof, and optionally one or more substances comprising water, chlorinating agent(s), catalyst(s), ester(s) of catalyst(s), and/or heavy byproduct(s), wherein the process comprises:

(a) providing a mixture comprising dichlorohydrin(s), one or more compounds selected from ester(s) of chlorohydrin(s), monochlorohydrin(s), and/or multihydroxylated-aliphatic hydrocarbon compound(s) and/or ester(s) thereof, and optionally one or more substances comprising water, chlorinating agent(s), catalyst(s), ester(s) of catalyst(s), and/or heavy byproduct(s);

(b) distilling or fractionating the mixture of step (a) in one or more unit operations to separate a lower boiling fraction comprising dichlorohydrin(s) and other lower boiling components present in the mixture from the mixture of step (a) to form a higher boiling fraction comprising the residue of the distillation or fractionation;

(c) introducing a stripping agent into the higher boiling fraction produced by step (b) for contact with the higher boiling fraction and stripping dichlorohydrin(s) from the higher boiling fraction into the stripping agent to produce a vapor fraction comprising dichlorohydrin(s) and stripping agent;

(d) recovering at least some of the lower boiling fraction of step (b) and the vapor fraction of step (c).

Another aspect of the present invention is a method for producing dichlorohydrin(s), wherein the mixture provided in step (a) is produced or derived from hydrochlorination of monochlorohydrin(s) and/or ester(s) thereof and/or multihydroxylated-aliphatic hydrocarbon compound(s) and/or ester(s) thereof.

Yet another aspect of the present invention is an apparatus suitable for producing dichlorohydrin(s) from multihydroxylated-aliphatic hydrocarbon compound(s) and/or ester(s) thereof comprising:

(1) at least one reactor;

(2) at least one separation device comprising at least one first liquid-vapor contacting device having a bottom end and a top end for applying a decreasing temperature gradient from the bottom end to the top end to substances within the first liquid-vapor contacting device; and (3) at least one second contacting device for contacting a liquid with a vapor-phase stripping agent, wherein the at least one reactor (1) is connected directly or indirectly to the at least one separation device (2) for conducting a reactor effluent feed stream (4) from the at least one reactor (1) to the at least one first liquid-vapor contacting device of the at least one separation device (2) for distillation and/or fractionation, the at least one separation device (2) is connected directly or indirectly to the at least one second liquid-vapor contacting device (3) for conducting a distilled or fractionated liquid residue feed stream (5) from the at least one first liquid-vapor contacting device of the at least one separation device (2) to the at least one second liquid-vapor contacting device (3) for stripping, the at least one separation device (2) having a first port (6) for recovering a dichlorohydrin(s)-containing distillate, and the at least one second liquid-vapor contacting device (3) is connected directly or indirectly to at least one source of stripping agent (7) for introducing one or more stripping agents into a distilled or fractionated liquid residue delivered to the second liquid-vapor contacting device (3) via liquid residue feed stream (5), the at least one second liquid-vapor contacting device (3) having at least one second port (8) for recovering a dichlorohydrin(s)-containing product stripped from a distilled or fractionated liquid residue delivered to the second liquid-vapor contacting device (3) via liquid residue feed stream (5).

BRIEF DESCRIPTION OF THE DRAWINGS

FIG. 1 is a process diagram illustrating one embodiment of the process of the present invention.

DETAILED DESCRIPTION OF THE INVENTION

Definitions

As used herein, the term "multihydroxylated-aliphatic hydrocarbon compound" (abbreviated hereafter as "MAHC") refers to a compound that contains at least two hydroxyl groups covalently bonded to two separate vicinal carbon atoms and no ether linking groups. They contain at least two sp3 hybridized carbons each bearing an OH group. The MAHCs include any vicinal-diol (1,2-diol) or triol (1,2,3-triol) containing hydrocarbon including higher orders of contiguous or vicinal repeat units. The definition of MAHC also includes for example one or more 1,3-1,4-, 1,5- and 1,6-diol functional groups as well. Geminal-diols, for example, are precluded from this class of MAHCs.

The MAHCs contain at least 2, preferably at least 3, up to about 60, preferably up to 20, more preferably up to 10, even more preferably up to 4, and yet more preferably up to 3, carbon atoms and can contain, in addition to aliphatic hydrocarbon, aromatic moieties or heteroatoms including for example halide, sulfur, phosphorus, nitrogen, oxygen, silicon, and boron heteroatoms; and mixtures thereof. The MAHCs may also be a polymer such as polyvinyl alcohol.

The terms "glycerin", "glycerol" and "glycerine", and esters thereof, may be used as synonyms for the compound 1,2,3-trihydroxypropane, and esters thereof.

As used herein, the term "chlorohydrin" means a compound containing at least one hydroxyl group and at least one chlorine atom covalently bonded to two separate vicinal aliphatic carbon atoms and no ether linking groups. Chlorohydrins are obtainable by replacing one or more hydroxyl groups of MAHCs with covalently bonded chlorine atoms via hydrochlorination. The chlorohydrins contain at least 2, and preferably at least 3, up to about 60, preferably up to 20, more preferably up to 10, even more preferably up to 4, and yet more preferably up to 3, carbon atoms and, in addition to aliphatic hydrocarbon, can contain aromatic moieties or heteroatoms including for example halide, sulfur, phosphorus, nitrogen, oxygen, silicon, and boron heteroatoms, and mixtures thereof. A chlorohydrin that contains at least two hydroxyl groups is also a MAHC.

As used herein, the term "monochlorohydrin" means chlorohydrin having one chlorine atom and at least two hydroxyl groups, wherein the chlorine atom and at least one hydroxyl group are covalently bonded to two separate vicinal aliphatic carbon atoms (referred to hereafter by the abbreviation "MCH"). MCH produced by hydrochlorination of glycerin or glycerin esters includes, for example, 3-chloro-1,2-propanediol and 2-chloro-1,3-propanediol.

As used herein, the term "dichlorohydrin" means chlorohydrin having two chlorine atoms and at least one hydroxyl group, wherein at least one chlorine atom and at least one hydroxyl group are covalently bonded to two separate vicinal aliphatic carbon atoms (referred to hereafter by the abbreviation "DCH"). Dichlorohydrins produced by hydrochlorination of glycerin or glycerin esters include 1,3-dichloro-2-propanol and 2,3-dichloro-1-propanol.

As used herein, the expression "under hydrochlorination conditions" means conditions capable of converting at least 1 wt. %, preferably at least 5 wt. %, more preferably at least 10 wt. % of MAHCs, MCHs, and esters of MAHCs and MCHs present in a mixture and/or feed stream into DCH(s) and/or ester(s) thereof.

As used herein, the term "byproduct(s)" means compound(s) that is/are not chlorohydrin(s) and/or ester(s) thereof and/or chlorinating agent(s) and that do not form chlorohydrin(s) and/or ester(s) thereof under the hydrochlorinating conditions selected according to the present invention.

The expression "heavy byproduct(s)" refer to oligomers of mixture (a) components, such as oligomers of MAHCs and/or esters thereof and oligomers of chlorohydrins and/or esters thereof, and derivatives of such oligomers, such as esters thereof, chlorinated oligomers, and/or chlorinated esters thereof, having a number average molecular weight equal to or greater than the number average molecular weight of the oligomer, such as chlorinated oligomers. The terms chlorohydrin(s), MCH(s) and DCH(s), and ester(s) thereof, are not intended to include heavy byproducts.

The term "epoxide" means a compound containing at least one oxygen bridge on a carbon-carbon bond. Generally, the carbon atoms of the carbon-carbon bond are contiguous and the compound can include other atoms than carbon and oxygen atoms, like hydrogen and halogens, for example. Preferred epoxides are ethylene oxide, propylene oxide, glycidol and epichlorohydrin.

As used herein, the expression, "liquid phase" refers to a continuous intermediate phase between gas phase and a solid phase that may optionally comprise a minor amount of gas and/or solid discrete phase(s). The liquid phase may comprise one or more immiscible liquid phases and may contain one or more dissolved solids, such as one or more acids, bases, or salts.

As used herein, the expression "vapor phase" refers to a continuous gaseous phase that may optionally comprise a minor amount of liquid and/or solid discrete phase(s) (e.g., aerosol). The vapor phase may be a single gas or a mixture, such as a mixture of two or more gases, two or more liquid discrete phases, and/or two or more solid discrete phases.

The expression "lower boiling fraction" refers to a fraction derived from the mixture provided in step (a) in which more than half the total quantity of components of the lower boiling fraction are components of the mixture, or derived from the mixture, that are more volatile under the conditions of the unit operation than the components of the higher boiling fraction in the same unit operation derived from the same mixture provided in step (a).

The expression "higher boiling fraction" refers to a fraction derived from the mixture provided in step (a) in which more than half the total quantity of components of the higher boiling fraction are components of the mixture, or derived from the mixture, that are less volatile than the components of the lower boiling fraction in the same unit operation derived from the same mixture provided in step (a).

As used herein, the expression "liquid-vapor contacting device" refers to devices that serve to provide the contacting and development of at least one interfacial surface between liquid and vapor in the device. Examples of liquid-vapor contacting devices include plate column, packed column, wetted-wall (falling film) column, spray chamber, heat exchanger or any combination thereof. Examples of devices comprising plate columns and packed columns include distillation columns, fractionation columns, and stripping columns.

As used herein, the term "condenser" means a non-adiabatic system for removing heat from a process fluid via a secondary fluid physically separated from the process fluid. The process fluid and the secondary fluid may each be a vapor, a liquid, or a combination of liquid and vapor. A condenser is generally associated with a section of a distillation or fractionation column. It may be a unit operation external to a distillation column or it may be a unit operation internal to a distillation column. The physical separation may be in the form of tubes and the condensation may be carried out on the inside or outside of the tubes. The condenser may take the form of cooling elements on the decks of distillation column fractionating trays or as cooling elements between distillation column packing beds.

Mixture (a):

Mixture (a) may be obtained directly or indirectly from any hydrochlorination process well-known in the art. For example, German Patent No. 197308 teaches a process for preparing a chlorohydrin by the catalytic hydrochlorination of glycerin by means of anhydrous hydrogen chloride. WO 2005/021476 discloses a continuous process for preparing the dichloropropanols by hydrochlorination of glycerin and/or monochloropropanediols with gaseous hydrogen chloride with catalysis of a carboxylic acid. WO 2006/020234 A1 describes a process for conversion of a glycerol or an ester or a mixture thereof to a chlorohydrin, comprising the step of contacting a MAHC, an ester of a MAHC, or a mixture thereof with a source of a superatmospheric partial pressure of hydrogen chloride to produce a chlorohydrin, an ester of a chlorohydrin, or a mixture thereof in the presence of an organic acid catalyst without substantially removing water. The above references are hereby incorporated herein by reference with respect to the above-described disclosures.

In an exemplifying hydrochlorination process, MAHC and a hydrochlorination catalyst are charged to the hydrochlorination reactor. Then a chlorinating agent such as hydrogen chloride is added to the reactor. The reactor pressure is adjusted to the desired pressure and the reactor contents are heated to the desired temperature for the desired length of time. After completion of the hydrochlorination reaction or while carrying out the hydrochlorination reaction, the reactor contents as a reaction effluent stream is discharged from the reactor and fed directly, or indirectly via another reactor or other intervening step, to a separation system comprising a DCH recovery system according to the present invention and optionally including other separation systems or equipment, such as a flash vessel and/or reboiler.

The hydrochlorination reaction above may be carried out in one or more hydrochlorination reactor vessels such as a single or multiple continuous stirred tank reactors (referred to hereafter by the abbreviation "CSTR"), single or multiple tubular reactor(s), plug flow reactors (referred to hereafter by the abbreviation "PFR"), or combinations thereof. The hydrochlorination reactor can be, for example, one reactor or multiple reactors connected with each other in series or in parallel including, for example, one or more CSTRs, one or more tubular reactors, one or more PFRs, one or more bubble column reactors, and combinations thereof.

In a preferred embodiment, part or all of the hydrochlorination effluent stream is a feed stream from a PFR. A PFR is a type of reactor that has a high length/diameter (L/D) ratio and has a composition profile along the length of the reactor. The concentration of the reactants being fed into the PFR decreases from inlet to the outlet along the flow path of the PFR and the concentration of DCHs increases from inlet to the outlet along the flow path of the PFR. In the case of hydrochlorination of glycerol, the concentration of HCl and glycerol decreases from inlet of the PFR to outlet of the PFR while the total concentration of 1,3-dichloro-2-propanol and 2,3-dichloro-1-propanol increases from inlet of the PFR to the outlet of the PFR.

The equipment useful for conducting the hydrochlorination reaction may be any well-known equipment in the art and should be capable of containing the reaction mixture at the conditions of the hydrochlorination. Suitable equipment may be fabricated of materials which are resistant to corrosion by the process components, and may include for example, metals such as tantalum, suitable metallic alloys (particularly nickel-molybdenum alloys such as Hastalloy C©), or glass-lined equipment, for example.

In addition to DCH(s), one or more of the unreacted MAHC(s) and/or chlorination agent(s), reaction intermediates such as MCH(s), MCH ester(s), and/or DCH ester(s), catalyst(s), ester(s) of catalyst(s), water, and/or heavy byproduct(s) may present in mixture (a). A recycle process is preferred in which one or more of the unreacted MAHC(s), ester(s) of MAHC(s) and/or chlorination agent(s), reaction intermediates such as MCH(s), MCH ester(s), DCH ester(s), and other substances such as catalyst(s), ester(s) of catalyst(s), and water are preferably recycled to a prior step in the process, such as to at least one hydrochlorination reactor for further hydrochlorination. In particular, a liquid higher boiling fraction comprising a residue of the stripping step containing one or more of MAHC(s), MCH(s), catalyst(s), and/or ester(s) of one or more MAHC(s), MCH(s), DCH(s) and/or catalyst(s), and preferably a combination of two or more thereof, is recycled to the hydrochlorination step, such as by recycling the higher boiling fraction to one or more reactor(s), Such recycle process(es) is preferably continuous. In this manner, raw material efficiencies are maximized and/or catalysts are reused.

When catalysts are reused in such a process scheme, it may be desirable to employ the catalysts in a higher concentration than they are employed in a single-pass process. This may result in faster reactions, or smaller process equipment, which results in lower capital costs for the equipment employed.

In a continuous recycle process, undesirable impurities and/or reaction byproducts may build up in the process. Thus, it is desirable to provide a means for removing such impurities from the process, such as via one or more purge outlets, for example, or by a separation step. Furthermore, a purged stream may be further treated to recover a useful portion of the purged stream.

The chlorinating agent that may optionally be present in the mixture treated according to the present invention is preferably hydrogen chloride or hydrogen chloride source, and may be a gas, a liquid or in a solution, or a mixture thereof. The hydrogen chloride is preferably introduced in the gaseous state and, when the hydrochlorination reaction mixture is in the liquid phase, at least some of the hydrogen chloride gas is preferably dissolved in the liquid reaction mixture. The hydrogen chloride may, however, be diluted in a solvent, such as an alcohol (for example methanol) or a chlorinated hydrocarbon, or in a carrier gas such as nitrogen, if desired.

It is preferred that the hydrochlorination step of the present invention be carried out under superatmospheric pressure conditions. "Superatmospheric pressure" herein means that the hydrogen chloride (HCl) partial pressure is above atmospheric pressure, i.e. 15 psia (103 kPa) or greater. Generally, the hydrogen chloride partial pressure employed in the hydrochlorination process is at least about 15 psia (103 kPa) or greater. Preferably, the hydrogen chloride partial pressure employed in the hydrochlorination process is not less than about 25 psia (172 kPa), more preferably not less than about 35 psia (241 kPa), and most preferably not less than about 55 psia (379 kPa); and preferably not greater than about 1000 psia (6.9 MPa), more preferably not greater than about 600 psia (4.1 MPa), and most preferably not greater than about 150 psia (1.0 MPa).

It is also preferred to conduct the hydrochlorination step at a temperature sufficient for hydrochlorination that is also below the boiling point of the chlorohydrin(s) in the reaction mixture having the lowest boiling point for a given pressure condition during the hydrochlorination step in order to keep the chlorohydrin(s) produced and converted during hydrochlorination in the liquid phase of the reaction mixture for recovery in steps (b) and (c). The upper limit of this preferred temperature range may be adjusted by adjusting the pressure condition. A higher pressure during hydrochlorination may be selected to increase the boiling point temperature of the chlorohydrin(s) in the reaction mixture, so that the preferred temperature range for keeping DCH(s) in the liquid phase may be increased by increasing the pressure condition.

Preferably, less than 50, more preferably less than 10, even more preferably less than 5, and yet more preferably less than 1, percent of the DCH present in the hydrochlorination effluent is removed from the hydrochlorination effluent prior to step (b).

The hydrochlorination effluent comprises one or more DCHs, one or more compounds comprising ester(s) of DCH(s), MCH(s) and/or ester(s) thereof, and MAHC(s) and/or ester(s) thereof, and optionally one or more substances comprising water, chlorination agent(s), catalyst(s) and/or ester(s) of catalyst(s). Additional optional components may also be present in the effluent depending on the starting materials, reaction conditions, and any process steps intervening between the hydrochlorination reaction and recovery of DCH according to the present invention. The hydrochlorination effluent is preferably in the liquid phase as the hydrochlorination effluent is withdrawn from the hydrochlorination step and/or reactor and the mixture provided in step (a) comprises at least part of the liquid phase effluent of the hydrochlorination step.

In a preferred embodiment, at least one MAHC and/or ester thereof is present in the mixture provided in step (a). When MAHC(s) and/or ester(s) thereof is/are present in the mixture provided in step (a), the same MAHC(s) and/or ester(s) thereof may also be present in the high-boiling fraction of step (b).

MAHCs found in the effluent treated according the present invention may include for example 1,2-ethanediol; 1,2-propanediol; 1,3-propanediol; 3-chloro-1,2-propanediol; 2-chloro-1,3-propanediol; 1,4-butanediol; 1,5-pentanediol; cyclohexanediols; 1,2-butanediol; 1,2-cyclohexanedimethanol; 1,2,3-propanetriol (also known as, and used herein interchangeable as, "glycerin", "glycerine", or "glycerol"); and mixtures thereof. Preferably, the MAHCs in the effluents treated according to the present invention include for example 1,2-ethanediol; 1,2-propanediol; 1,3-propanediol; and 1,2,3-propanetriol; with 1,2,3-propanetriol being most preferred.

Examples of esters of MAHCs found in the effluents treated according to the present invention include for example ethylene glycol monoacetate, propanediol monoacetates, glycerin monoacetates, glycerin monostearates, glycerin diacetates, and mixtures thereof. In one embodiment, such esters can be made from mixtures of MAHC with exhaustively esterified MAHC, for example mixtures of glycerol triacetate and glycerol.

In the same or another preferred embodiment, at least one MCH and/or ester thereof is present in the mixture provided in step (a). When MCH(s) and/or ester(s) thereof is/are present in the mixture provided in step (a), the same MCH(s) and/or ester(s) thereof may also be present in the high-boiling fraction of step (b).

The MCHs generally correspond to the hydrochlorinated MAHCs in which one of a pair of hydroxyl groups covalently bonded to two separate vicinal carbon atoms is replaced by a covalently bonded chlorine atom. The ester(s) of MCH may be the result of hydrochlorination of MAHC ester(s) or reaction with an acid catalyst, for example.

The DCHs generally correspond to the hydrochlorinated MAHCs in which two hydroxyl groups covalently bonded to two separate carbon atoms, at least one of which is vicinal to a third carbon atom having a hydroxyl group, are each replaced by a covalently bonded chlorine atom. The ester(s) of DCH may be the result of hydrochlorination of MAHC ester(s), MCH ester(s) or reaction(s) with acid catalyst(s), for example.

In an embodiment of the present invention where MAHC(s) is/are the starting material fed to the process, as opposed to ester(s) of MAHC(s) or a mixture of MAHC(s) and ester(s) thereof as a starting material, it is generally preferred that the formation of chlorohydrin be promoted by the presence of one or more catalyst(s) and/or ester(s) thereof. Catalyst(s) and/or ester(s) thereof may also be present where ester(s) of MAHC(s), or a mixture of MAHC(s) and ester(s) thereof, is a starting material to further accelerate the hydrochlorination reaction.

Carboxylic acids, RCOOH, catalyze the hydrochlorination of MAHCs to chlorohydrins. The specific carboxylic acid catalyst chosen may be based upon a number of factors including for example, its efficacy as a catalyst, its cost, its stability to reaction conditions, and its physical properties. The particular process, and process scheme in which the catalyst is to be employed may also be a factor in selecting the particular catalyst. The "R" groups of the carboxylic acid may be independently chosen from hydrogen or hydrocarbyl groups, including alkyl, aryl, aralkyl, and alkaryl. The hydrocarbyl groups may be linear, branched or cyclic, and may be substituted or un-substituted. Permissible substituents include any functional group that does not detrimentally interfere with the performance of the catalyst, and may include heteroatoms. Non-limiting examples of permissible functional groups include chloride, bromide, iodide, hydroxyl, phenol, ether, amide, primary amine, secondary amine, tertiary amine, quaternary ammonium, sulfonate, sulfonic acid, phosphonate, and phosphonic acid.

The carboxylic acids useful as hydrochlorination catalysts may be monobasic such as acetic acid, formic acid, propionic acid, butyric acid, isobutyric acid, hexanoic acid, 4-methylvaleric acid, heptanoic acid, oleic acid, or stearic acid; or polybasic such as succinic acid, adipic acid, or terephthalic acid. Examples of aralkyl carboxylic acids include phenylacetic acid and 4-aminophenylacetic acid. Examples of substituted carboxylic acids include 4-aminobutyric acid, 4-dimethylaminobutyric acid, 6-aminocaproic acid, 6-hydroxyhexanoic acid, 6-chlorohexanoic acid, 6-aminohexanoic acid, 4-aminophenylacetic acid, 4-hydroxyphenylacetic acid, lactic acid, glycolic acid, 4-dimethylaminobutyric acid, and 4-trimethylammoniumbutyric acid. Additionally, materials that can be converted into carboxylic acids under reaction conditions, including for example carboxylic acid halides, such as acetyl chloride, 6-chlorohexanoyl chloride, 6-hydroxyhexanoyl chloride, 6-hydroxyhexanoic acid, and 4-trimethylammonium butyric acid chloride; carboxylic acid anhydrides such as acetic anhydride and maleic anhydride; carboxylic acid esters such as methyl acetate, methyl propionate, methyl pivalate, methyl butyrate, ethylene glycol monoacetate, ethylene glycol diacetate, propanediol monoacetates, propanediol diacetates, glycerin monoacetates, glycerin diacetates, glycerin triacetate, and glycerin esters of a carboxylic acid (including glycerin mono-, di-, and tri-esters); MAHC acetates such as glycerol 1,2-diacetate; carboxylic acid amides such as ε-caprolactam and γ-butyrolactam; and carboxylic acid lactones such as γ-butyrolactone, δ-valerolactone and ε-caprolactone may also be employed in the present invention. Zinc acetate is an example of a metal organic compound. Mixtures of the foregoing catalysts and catalyst precursors may also be used.

When a catalyst is used in the superatmospheric pressure process, the catalyst may be for example a carboxylic acid; an anhydride; an acid chloride; an ester; a lactone; a lactam; an amide; a metal organic compound such as sodium acetate; or a combination thereof. Any compound that is convertible to a carboxylic acid or a functionalized carboxylic acid under hydrochlorination reaction conditions may also be used. A preferred carboxylic acid for the superatmospheric pressure process is an acid with a functional group consisting of a halogen, an amine, an alcohol, an alkylated amine, a sulfhydryl, an aryl group or an alkyl group, or combinations thereof, wherein this moiety does not sterically hinder the carboxylic acid group.

Certain catalysts may also be advantageously employed at superatmospheric, atmospheric or sub-atmospheric pressure, and particularly in circumstances where water is continuously or periodically removed from the reaction mixture to drive conversion to desirably higher levels as may be the case when recovering DCH(s) according to the claimed invention. For example, the hydrochlorination of MAHC(s) reaction can be practiced by introducing hydrogen chloride gas into contact with a mixture of MAHC(s) and catalyst(s), such as by sparging the hydrogen chloride gas through a liquid phase reaction mixture. In such a process, the use of less volatile catalysts, such as 6-hydroxyhexanoic acid, 4-aminobutyric acid; dimethyl 4-aminobutyric acid; 6-chlorohexanoic acid; caprolactone; carboxylic acid amides such as ε-caprolactam and γ-butyrolactam; carboxylic acid lactones such as γ-butyrolactone, δ-valerolactone and ε-caprolactone; caprolactam; 4-hydroxyphenyl acetic acid; 6-amino-caproic acid; 4-aminophenylacetic acid; lactic acid; glycolic acid; 4-dimethylamino-butyric acid; 4-trimethylammoniumbutyric acid; and combination thereof; and the like may be preferred. It is most desirable to employ a catalyst, under these atmospheric or subatmospheric conditions, that is less volatile than the DCH(s) produced and recovered.

Preferred catalysts used in the present invention include carboxylic acids, esters of carboxylic acids, and combinations thereof, particularly esters and acids having a boiling point higher than that of the desired highest boiling DCH that is formed in the reaction mixture (i.e., the catalyst(s) is/are preferably less volatile than the DCH(s) in the mixture), so that the DCH(s) can be removed without removing the catalyst. Catalysts which meet this definition and are useful in the present invention include for example, polyacrylic acid, glycerin esters of carboxylic acids (including glycerin mono-, di-, and tri-esters), polyethylene grafted with acrylic acid, divinylbenzene/methacrylic acid copolymer, 6-chlorohexanoic acid, 4-chlorobutanoic acid, caprolactone, heptanoic acid, 4-hydroxyphenylacetic acid, 4-aminophenylacetic acid, 6-hydroxyhexanoic acid, 4-aminobutyric acid, 4-dimethylaminobutyric acid, 4-trimethyl-ammoniumbutyric acid chloride, stearic acid, 5-chlorovaleric acid, 6-hydroxyhexanoic acid, 4-aminophenylacetic acid, and mixtures thereof. Carboxylic acids that are sterically unencumbered around the carboxylic acid group are generally preferred.

Furthermore, the catalyst(s) is/are preferably miscible with the MAHC(s) employed. For this reason, the catalyst(s) may contain polar heteroatom substituents such as hydroxyl, amino or substituted amino, or halide groups, which render the catalyst miscible with the MAHC(s) in the reaction mixture, such as glycerol.

One embodiment of the catalyst that may be present is generally represented by Formula (a) shown below wherein the functional group "R'" includes a functional group comprising an amine, an alcohol, a halogen, a sulfhydryl, an ether; or an alkyl, an aryl or alkaryl group of from 1 to about 20 carbon atoms containing said functional group; or a combination thereof; and wherein the functional group "R" may include a hydrogen, an alkali, an alkali earth or a transition metal or a hydrocarbon functional group.

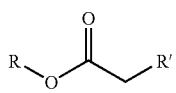

Formula (a)

Where the catalyst is recycled and used repeatedly, such recycled catalysts may be present in an amount from about 0.1 mole %, preferably from about 1 mole %, more preferably from about 5 mole %, up to about 99.9 mole %, preferably up to 70 mol %, and more preferably up to 50 mole %, based on the amount in moles of MAHC present. Higher catalysts concentrations may be desirably employed to reduce the reaction time and minimize the size of process equipment.

In a preferred embodiment, the mixture (a) comprises water, such as the water produced as a byproduct of the hydrochlorination reaction, water present in the starting materials for the hydrochlorination reaction, and/or water introduced as the stripping agent. The mixture (a) may contain at least 1, more preferably at least 5, weight-percent water up to 90, more preferably up to 50, weight-percent water.

The mixture of step (a) may be a combination of liquid phase and vapor phase. The mixture of step (a) is preferably provided to the separation step as a liquid phase as opposed to a gaseous or vapor phase.

In one embodiment, the mixture of step (a) is provided to step (b) by separating a hydrochlorination reaction effluent stream into a vapor-phase effluent stream and a liquid-phase effluent stream prior to step (b) and introducing the liquid-phase effluent stream or both the vapor-phase effluent stream and the liquid-phase effluent stream, separately or combined, into step (b). The separation of the reaction effluent stream may be carried out in, for example, a flash vessel separate from or integral with step (b).

Recovery of DCH from the mixture (a):

Recovery of DCH according to the present invention takes place in two steps. First, the mixture (a) is distilled and/or fractionated to separate a lower boiling fraction comprising dichlorohydrin(s) from the mixture of step (a) to form a higher boiling fraction comprising the residue of the distillation or fractionation. DCH(s), and preferably water, may be recovered from the lower boiling fraction of step (b).

Then the residue of the distillation and/or fractionation is stripped (c) by introducing at least one stripping agent into contact with the higher boiling fraction produced by step (b) for stripping dichlorohydrin(s) from the higher boiling fraction with the at least one stripping agent to produce a vapor fraction enriched with DCH(s) and the at least one stripping agent. Stripping step (c) is preferably carried out on the higher boiling fraction produced in step (b) after removing the higher boiling fraction produced in step (b) from the distillation or fractionation step (b).

Since the distillation residue is stripped in stripping step (c), step (b) may be conducted under milder separation conditions than those required to optimize DCH recovery. DCH(s), and preferably water, may be recovered from the lower boiling fraction of step (b). The temperature and pressure for step (b) are preferably adjusted to recover at least 1, more preferably at least 10, even more preferably at least 25, and yet more preferably at least 50, and up to 99, more preferably up to 95, yet more preferably up to 90, yet even more preferably up to 80, and even more preferably up to 70, weight-percent of the total amount of DCH in the mixture provided in step (a) via the lower boiling fraction produced in step (b).

Milder separation conditions may include reducing the temperature of the distillation bottoms to reduce energy consumption and reduce the rate of heavy byproduct formation during step (b). Safety and efficiency are improved when the distillation column is operated at lower bottom temperature.

Distillation or fractionation step (b) is preferably carried out at a temperature measured in the distillation bottoms of at least 25° C., more preferably at least 50° C., yet more preferably at least 80° C., even more preferably at least 100° C., and yet even more preferably at least 110° C., up to 200° C., more preferably up to 160° C., yet more preferably up to 140° C., even more preferably up to 139° C., yet even more preferably up to 135° C., yet even more preferably up to 132° C., yet even more preferably up to 125° C., and yet even more preferably up to 120° C.

Milder separation conditions may also include operation of step (b) under pressure conditions higher than those used in conventional processes for separating DCH(s) from reactor effluents. The higher pressure condition process allows for energy savings and a wider selection of vacuum devices. A more economical steam-jet ejector or vacuum pump can be used, which reduces fixed capital and operating costs. Operational reliability is also improved through the use of steam-jet ejectors, because steam-jet ejectors do not have moving parts, while low pressure, high vacuum operation generally requires the use of rotary oil-sealed vacuum pumps or multiple stages of steam-jet ejectors. Also higher distillation column pressure operation reduces column size, thereby reducing the capital investment to be amortized.

The distillation or fractionation step (b) is preferably carried out at a pressure of at least 0.1 kPa, more preferably at least 1 kPa, even more preferably at least 3 kPa, yet more preferably at least 6 kPa, and even more preferably at least 10 kPa, up to 1 MPa, more preferably up to 0.12 MPa, yet more preferably up to 0.05 MPa, and even more preferably up to 0.02 MPa.

The percent DCH(s) recovered from the mixture introduced into step (b) generally depends on the combination of temperature and pressure conditions selected. To obtain a given DCH recovery in step (b), a reduction in temperature generally requires a reduction in operating pressure and an increase in operating pressure, conversely, generally requires an increase in operating temperature. The specific temperature and pressure conditions selected will depend on the extent to which realization of the respective benefits relating to low temperature and higher pressure operation is desired.

Step (b) is preferably carried out under conditions such that the amount of heavy byproducts in the high boiling fraction of step (b) does not exceed 110 percent, more preferably not more than 108 percent, even more preferably not more than 105 percent, and even more preferably not more than 102 percent, of the amount of heavy byproducts in the mixture provided in step (a).

The conditions during step (b) are preferably adjusted to produce a higher boiling fraction containing less than 50, more preferably less than 20, even more preferably less than 10, and yet even more preferably less than 5, percent of the chlorinating agent(s) present in the mixture provided in step (a). One or more conditions of step (b), such as the temperature and pressure, may be adjusted to remove chlorinating agent(s) from the mixture (a) provided to step (b).

When the chlorinating agent is hydrogen chloride for example, the hydrogen chloride may be removed from the mixture (a) during step (b) by maintaining a pressure during step (b) that is below the pressure required to maintain dissolution of the hydrogen chloride present in the mixture provided in step (a) and/or maintaining a temperature during step (b) that is greater than the temperature required to maintain dissolution of the hydrogen chloride present in the mixture provided in step (a).

In a preferred embodiment, the mixture provided in step (a) is passed through a pressure letdown step for degassing the mixture prior to distilling and/or fractionating the mixture. When there are flow fluctuations or surges upstream from the distillation and/or fractionation step, the pressure letdown step and/or a surge vessel may also be used to help regulate the flow of the mixture into the distillation and/or fractionation step.

Step (b) is preferably carried out in a distillation column, such as a fractional distillation column. Examples of suitable distillation columns include a plate or tray columns, bubble cap columns and packed columns.

In one embodiment, additional MAHC(s) and/or ester(s) thereof may be introduced into step (b) for reactive distillation/fractionation. The additional MAHC(s) and/or ester(s) thereof may react with the chlorination agent to produce additional MCH(s) and/or ester(s) thereof. Additional MAHC(s) may also react with ester(s) of DCH(s) and MCH(s) to convert them to non-ester(s) to facilitate recovery of DCH(s). The additional MAHC(s) and/or ester(s) thereof is/are preferably introduced as a liquid phase into a reflux to provide additional liquid phase for reflux.

In a preferred embodiment, step (b) comprises:
(b1) vaporizing an azeotropic mixture of DCH(s) and water from the mixture of step (a) to separate a lower boiling fraction comprising at least DCH(s) and water from the mixture of step (a) and
(b2) condensing the low boiling fraction of step (b1) to form a liquid aqueous phase and a liquid organic phase comprising DCH(s).

The condensing step (b2) may comprise refluxing in a distillation column, such as a fractional distillation column and/or a packed distillation column.

In one embodiment, additional MAHC(s) and/or ester(s) thereof may be introduced into condensing step (b2) for reactive distillation/fractionation for the reasons stated above. Such addition also increases the amount of liquid available for reflux during distillation/fractionation, which increases the efficiency with which step (b) separates DCH and water from the other components of the mixture (a) provided to step (b).

Step (b) may further comprise:
(b3) separating the liquid aqueous phase of step (b2) from the liquid organic phase of step (b2) and
(b4) recycling at least some of the liquid aqueous phase of step (b3) to step (b1) and/or step (b2).

Recycling the liquid aqueous phase to step (b1) may be used to facilitate recovery of DCH by azeotroping and/or stripping DCH(s) from the reaction mixture.

Recycling the liquid aqueous phase to step (b2) may be used to provide additional liquid for reflux during step (b). When sufficient liquid aqueous phase is recycled to step (b2), the liquid aqueous phase may flow to the bottom of the distillation/fraction apparatus, so that at least some of the same liquid aqueous phase is also recycled to step (b1) where it may also facilitate recovery of DCH by azeotroping and/or stripping DCH(s) from the reaction mixture.

In step (c), a stripping agent is introduced into the higher boiling fraction produced by step (b). Preferred stripping agents include steam, nitrogen, methane and carbon dioxide, and mixtures thereof.

The stripping agent is preferably an azeotroping agent for the DCH(s) in the high boiling fraction produced in step (b). Such stripping agents include steam. Superheated steam is more preferred.

The stripping agent is preferably introduced into the higher boiling fraction at a temperature equal to or greater than the temperature of the higher boiling fraction during step (b) and is preferably introduced at a temperature equal to or greater than the boiling point of the DCH and water azeotrope at the pressure condition of step (c). The stripping agent is preferably introduced into the higher boiling fraction at a temperature that is greater, such as at least 10° C., or 20° C., or 30° C. greater, than the temperature of the higher boiling fraction to compensate for heat loss during step (c) and thereby maintain the high boiling fraction at the desired elevated temperature.

Step (c) is preferably carried out at a high boiling fraction temperature of at least 25° C., more preferably at least 100° C., up to 140° C., and more preferably up to 130° C. and at a pressure of at least 14 kPa, preferably at least 21 kPa, up to 0.2 MPa, more preferably up to 0.1 MPa, and even more preferably up to 50 kPa. For economic reasons, step (c) may be carried out at atmospheric pressure.

Step (c) may further comprise distilling or fractionating the vapor fraction of step (c) for isolating dichlorohydrin(s) and stripping agent.

One or more stripping agents may also be introduced into the higher boiling fraction of step (b) while the same higher boiling fraction is distilled or fractionated according to step (b) for contact with the higher boiling fraction undergoing distillation or fractionation and stripping DCH(s) from the higher boiling fraction. The above description of preferred stripping agents and preferred conditions for introduction into step (c) apply to the introduction of stripping agent(s) during step (b).

The lower boiling fraction produced by step (b) and the vapor fraction produced in step (c) recovered in step (d) may be recovered separately and subjected to further processing steps or they may be combined. Depending on the further processing steps, the lower boiling fraction and/or the vapor fraction may be used separately or combined to supply DCHs for chemical conversion into other compounds without further processing. The lower boiling fraction/vapor fraction mixture may be used in used in processes for conversion of DCH(s) into other industrially useful chemical products.

The lower boiling fraction and/or the vapor fraction recovered in step (d) may, for example, be subjected to epoxidation to form epichlorohydrin without additional purification of the dichlorohydrin(s) other than via the above-described optional liquid-liquid phase separation for recycling an aqueous phase in step (b3) or via the above-described optional distillation or fractionation of the vapor fraction produced during step (c). An advantage of the present invention is that the steam introduced in step (c) not only improves DCH recovery, but also provides water to the downstream epoxidation process for keeping the concentration of sodium chloride formed during epoxidation at a concentration below saturation to avoid undesirable sodium chloride crystallization during epoxidation.

Any combination of the above process steps may be carried out independently or simultaneously with one another. In a preferred embodiment, one or more of the above process steps is carried out simultaneously with one another.

One or more of the above process steps may be carried out continuously or discontinuously. One or more of the above process steps are preferably carried out continuously (i.e., without interruption) for a time period of at least one hour. Preferably, all the above process steps are carried out continuously for a time period of at least one hour.

At least some of the higher boiling fraction treated in step (c) is preferably recycled to a hydrochlorination step. In a more preferred embodiment, substantially all the higher boiling fraction treated in step (c) is recycled to a hydrochlorination step. The hydrochlorination step is preferably the first step in the hydrochlorination process used to produce a hydrochlorination effluent containing components of the mixture (a).

Recycling the treated higher boiling fraction permits further reaction of MAHC(s) and/or ester(s) thereof and/or MCH(s) and/or ester(s) thereof to form additional DCH, which generally increases the overall hydrochlorination conversion and recovery rates. In that case, the process according to the present invention may recover at least 80 percent, more preferably at least 90 percent, even more preferably at least 95 percent, yet more preferably at least 99 percent, and yet even more preferably at least 99.9 percent of the DCH(s) produced during hydrochlorination.

The above process may be conducted using an apparatus according to the present invention. The apparatus is now described in more detail in reference to FIG. 1.

FIG. 1 is a block diagram showing the main features of an illustrative apparatus that may be used and their respective feed streams. The apparatus comprises at least one reactor (1); at least one separation device (2) comprising at least one first liquid-vapor contacting device having a bottom end and a top end for applying a gradually decreasing temperature gradient from the bottom end to the top end to substances within the column; and at least one second liquid-vapor contacting device (3) for contacting a liquid phase material with a stripping agent.

The at least one reactor (1) may be selected from various known reactors, such as CSTRs, tubular reactors, and PFRs, and combinations thereof. When multiple reactors are present, the reactors may be connected to each other in series or parallel. At least one reactor (1) is connected directly or indirectly to a first feed stream (12) comprising MAHC(s) and a second feed stream (13) comprising chlorinating agent.

The at least one reactor (1) is connected directly or indirectly to the at least one separation device (2) for conducting at least part of a reactor effluent feed stream (4) from the at least one reactor (1) to the at least one first liquid-vapor contacting device of separation device (2) for distillation and/or fractionation. The connection for conducting a reactor effluent feed stream (4) from the at least one reactor (1) is preferably adapted to conduct a liquid-phase feed stream from the at least one reactor (1).

The at least one separation device (2) comprises a first port (6) for recovering an effluent stream comprising DCH(s) separated from the reactor effluent feed stream (4) via the at least one first liquid-vapor contacting device of separation device (2) and preferably comprises a first vent (14) for removing gases at the top of the at least one first liquid-vapor contacting device of the separation device (2).

The at least one separation device (2) preferably comprises a means for applying a vacuum to the at least one first liquid-vapor contacting device of the at least one separation device (2) for reducing the pressure in the at least one column (2) below ambient atmospheric pressure. The means is preferably a steam-jet ejector.

The at least one first liquid-vapor contacting device of the at least one separation device (2) is preferably a distillation or fractionation column, such as a packed distillation column and/or a distillation column adapted for carrying out fractional distillation under reflux conditions having a reflux zone for carrying out reflux.

The at least one separation device (2) preferably comprises at least one flash vessel and the at least one reactor (1) is connected to at least one first liquid-vapor contacting device of the at least one separation device (2) via the at least one flash vessel, whereby the feed stream conducted from the reactor (1) is separated into a vapor phase and a liquid phase in the flash vessel by reducing the pressure on the liquid phase and the separated liquid phase is introduced into the first liquid-vapor contacting device of separation device (2) for distillation or fractionation.

The at least one separation device (2) also preferably comprises a reboiler connected to the at least one first liquid-vapor contacting device of the at least one separation device (2) for heating the feed stream(s) conducted to the at least one first liquid-vapor contacting device of the at least one separation device (2).

The at least one separation device (2) is connected directly or indirectly to the at least one second liquid-vapor contacting device (3) for conducting a distilled or fractionated liquid bottoms feed stream (5) from the at least one first liquid-vapor contacting device of the separation device (2) to the at least one second liquid-vapor contacting device (3) for stripping.

The at least one separation device (2) has a first port (6) for recovering a dichlorohydrin(s)-containing distillate.

The at least one second liquid-vapor contacting device (3) is connected directly or indirectly to at least one source of stripping agent (7) for introducing one or more stripping agents into a distilled or fractionated liquid residue delivered to the second liquid-vapor contacting device (3) via liquid residue feed stream (5), the at least one second liquid-vapor contacting device (3) having at least one second port (8) for recovering a dichlorohydrin(s)-containing product stripped from a distilled or fractionated liquid residue delivered to the second liquid-vapor contacting device (3) via liquid residue feed stream (5). The second liquid-vapor contacting device (3) preferably has a third port (9) for withdrawing stripped liquid residue feed stream from the second liquid-vapor contacting device (3).

The third port (9) is preferably connected to the at least one reactor (1) via recycle conduit (10) for conducting a recycle feed stream comprising a distillation- and stripper-treated fraction from the at least one second liquid-vapor contacting device (3) to the at least one reactor (1). The recycle conduit (10) preferably has a purge (11) for removal of heavy byproducts from the recycle feed stream.

The second liquid-vapor contacting device (3) is preferably a column and is more preferably a distillation column. The distillation column is preferably adapted for carrying out fractional distillation under reflux conditions having a reflux zone for carrying out reflux. Stripper effluent stream (8) is preferably a distillate obtainable with such a distillation column.

The second liquid-vapor contacting device (3) preferably has a second vent (15) for conducting a vapor phase effluent from the top of the second liquid-vapor contacting device (3).

The second liquid-vapor contacting device (3) is preferably a steam stripper.

To the extent that components of the above apparatus are exposed to corrosive materials, such components are preferably fabricated of materials which are resistant to corrosion by the process components. *Kirk-Othmer Encyclopedia of Chemical Technology*, $2^{nd}$ Edition (John Wiley and Sons, 1966), volume 11, pages 323-327, presents an extensive discussion of the corrosion resistance of metals and non-metals that can be used in hydrochloric acid and hydrogen chloride service. Specific examples of suitable materials are disclosed in WO 2006/020234. Specific examples include metals such as tantalum, suitable metallic alloys (particularly nickel-molybdenum alloys such as Hastalloy C©), or glass-lined equipment.

When milder temperature conditions are used to recover DCH according to the present invention, less expensive corrosion-resistant materials may be used in one or more components of the apparatus downstream from the reactor(s), such as distillation or fractionation column(s) (2), the second liquid-vapor contacting device (3) and/or components and conduits linking those components to each other or to other downstream components. This reduces the capital investment cost for building a production facility to be amortized, which reduces the overall cost of the process according to the present invention.

The following examples are for illustrative purposes only and are not intended to limit the scope of the present invention.

Equipment Used in the Examples

Distillation is carried out using a glass distillation column packed with 6 mm ceramic Intalox saddles, containing two packed bed sections. Feed to the column is located between the two packed bed sections. The column is provided with a glass reboiler and two partial condensers in series, also made of glass, for cooling the vapor stream exiting the column. The first condenser is cooled with chilled glycol. A portion of the condensate from the first condenser is returned to the column as reflux and the rest of the condensate is collected as product.

Uncondensed vapors from the first condenser are condensed in the second condenser operating at a lower temperature and cooled with chilled glycol. The uncondensed vapors exiting the second condenser are passed through a set of cold traps before entering the vacuum pump which provides vacuum to the whole system. The second condensed liquid-phase effluent from the second condenser is collected as product.

In Example 1, the distillation residue is fed to a steam stripping column. The steam stripping column has dimensions similar to those of the above-described distillation column.

Composition and Conditions of Feed Stream Mixture (a)

The feed stream composition and conditions shown in Table 1 below are used to provide the mixture (a) for each example:

TABLE 1

| Conditions and Composition | | Units |
|---|---|---|
| Feed Rate | 2.5 | kg/hr |
| Feed Temperature | 100 | ° C. |
| Feed Pressure | 790.8 | kPa |
| Feed Composition: | | |
| Hydrogen chloride | 3.7 | Weight-percent |
| Water | 8.4 | Weight-percent |
| 1,3-dichloro-2-propanol | 38.7 | Weight-percent |
| 2,3-dichloro-1-propanol | 4.9 | Weight-percent |
| 3-chloro-1,2-propanediol | 9.1 | Weight-percent |
| 2-chloro-1,3-propanediol | 10.8 | Weight-percent |
| Esters | 5.4 | Weight-percent |
| Glycerol | 19.0 | Weight-percent |

As shown in Table 1, the 1,3-dichloro-2-propanol rate is 38.7 weight-percent of the 2.5 kg/hr feed rate or 0.97 kg/hr and the 2,3-dichloro-1-propanol rate is 4.9 weight-percent of the 2.5 kg/hr feed rate or 0.12 kg/hr. The sum of the 1,3-dichloro-2-propanol feed rate (0.97 kg/hr) and 2,3-dichloro-1-propanol feed rate (0.12 kg/hr), is 1.09 kg/hr.

EXAMPLE 1

In this example, a DCH recovery process is carried out according to the present invention using the feed composition and conditions shown in Table 1. Distillation is carried out under moderate vacuum conditions followed by steam stripping.

The distillation column process conditions used in Example 1 are shown in Table 2 below:

TABLE 2

| Distillation Column Process Conditions | | Units |
|---|---|---|
| Condenser temperature | 47.1 | ° C. |
| Condenser pressure | 6.7 | kPa |
| Bottom temperature | 131.4 | ° C. |
| Reflux ratio (reflux rate/distillate rate) | 0.36 | |
| Distillate to feed ratio | 0.50 | |
| Distillate mass vapor fraction | 0.25 | |
| Pressure drop across the column | 1.3 | kPa |

Using a computer simulation based on actual data obtained in Comparative Example 1, the distillation data shown in Table 3 are obtained.

TABLE 3

| Subject | Vent | Aqueous Overhead | Organic Overhead | Bottoms | Units |
|---|---|---|---|---|---|
| Rate | 0.03 | 0.18 | 0.83 | 1.39 | kg/hr |
| HCl | 68.19 | 29.35 | 2.01 | — | wt. % |
| H$_2$O | 20.56 | 68.68 | 9.29 | — | wt. % |
| 1,3-dichloro-2-propanol | 10.85 | 1.87 | 81.65 | 15.85 | wt. % |
| 2,3-dichloro-1-propanol | 0.41 | 0.10 | 7.02 | 4.37 | wt. % |
| 3-chloro-1,2-propanediol | — | — | 0.01 | 16.31 | wt. % |
| 2-chloro-1,3-propanediol | — | — | 0.01 | 19.48 | wt. % |
| glycerin | — | — | — | 34.28 | wt. % |

"Vent" refers to stream 14 in FIG. 1. "Aqueous Overhead" refers to the aqueous phase of a two-phase liquid-liquid decanter used to separate overhead stream 6 of FIG. 1 after condensation. "Organic Overhead" refers to the organic phase of a two-phase liquid-liquid decanter used to separate overhead stream 6 of FIG. 1 after condensation. "Bottoms" refers to the distillation residue stream 5 of FIG. 1. Hyphen ("-") indicates that the weight-percent value was below 0.01.

The rate at which DCH is recovered in the overhead via distillation step (b) may be calculated as the difference between the DCH feed rate (1.09 kg/hr as shown in the explanation for Table 1) and the DCH bottom rate (0.28 kg/hr) or 0.81 kg/hr.

DCH recovery is therefore 74.3 percent (0.81÷1.09×100).

The distillation residue, referred to as the "bottoms" in Table 2, is used as the feed stream for computer simulated steam stripping based on the above described steam stripping column fed at the bottom with steam at a pressure of 1480 kPa and at a temperature of 197.7° C. at a rate of 1.0 kg/hr. The simulated column pressure is kept at 13.3 kPa. The results obtained are shown below in Table 4.

TABLE 4

| Subject | Aqueous Overhead | Organic Overhead | Bottoms | Units |
|---|---|---|---|---|
| Rate | 1.15 | 0.07 | 1.17 | kg/hr |
| H$_2$O | 81.57 | 17.34 | 4.29 | wt. % |
| 1,3-dichloro-2-propanol | 15.01 | 66.24 | 0.30 | wt. % |
| 2,3-dichloro-1-propanol | 3.41 | 16.42 | 0.91 | wt. % |
| 3-chloro-1,2-propanediol | — | — | 19.32 | wt. % |
| 2-chloro-1,3-propanediol | — | — | 23.07 | wt. % |
| glycerin | — | — | 40.60 | wt. % |

From the above data, the DCH bottom rate may be calculated by adding the weight-percent values for 1,3-dichloro-2-propanol and 2,3-dichloro-1-propanol, dividing the sum by 100, and multiplying the resulting value with the 1.17 kg/hr bottom rate to obtain 0.015 kg/hr.

Table 5 shows the combined overhead recovery rate and composition for distillation and steam stripping based on the data in Tables 3 and 4 above.

TABLE 5

| Subject | Total Recovered in Overhead | Units |
|---|---|---|
| Rate | 2.05 | kg/hr |
| H$_2$O | 49.34 | wt. % |
| 1,3-dichloro-2-propanol | 45.20 | wt. % |
| 2,3-dichloro-1-propanol | 5.39 | wt. % |

DCH recovery obtained with the distillation combined with steam stripping is 98.6 percent (1.075÷1.09×100).

Comparative Example

In this comparative example, DCH recovery is determined based on the conventional high vacuum distillation process using the Example 1 distillation equipment and distillation feed stream. The distillation conditions are modified to maximize DCH recovery during distillation by reducing the condenser pressure and adjusting the condenser temperature to take the lower condenser pressure into account while maintaining the same bottom temperature as shown below in Table 6.

TABLE 6

| Distillation Column Process Conditions | | Units |
|---|---|---|
| Condenser temperature | 9 | ° C. |
| Condenser pressure | 1.8 | kPa |
| Bottom temperature | 131.4 | ° C. |
| Reflux ratio (reflux rate/distillate rate) | 0.37 | |
| Distillate to feed ratio | 0.50 | |
| Distillate mass vapor fraction | 0.25 | |
| Pressure drop across the column | 1.3 | kPa |

The data obtained with the feed of Table 2 under the above distillation conditions is shown below in Table 7.

TABLE 7

| Subject | Vent | Aqueous Overhead | Organic Overhead | Bottoms | Units |
|---|---|---|---|---|---|
| Rate | 0.03 | 0.24 | 1.08 | 1.15 | kg/hr |
| HCl | 68.25 | 29.35 | 0.02 | — | wt. % |
| H$_2$O | 20.57 | 68.68 | 3.44 | — | wt. % |
| 1,3-dichloro-2-propanol | 10.64 | 1.83 | 86.24 | 2.48 | wt. % |
| 2,3-dichloro-1-propanol | 0.54 | 0.13 | 10.28 | 1.03 | wt. % |
| 3-chloro-1,2-propanediol | — | — | 0.01 | 19.73 | wt. % |
| 2-chloro-1,3-propanediol | — | — | 0.01 | 23.56 | wt. % |
| glycerin | — | — | — | 41.46 | wt. % |

The DCH overhead rate may be calculated as 1.05 kg/hr (1.09 kg/hr DCH feed rate minus 0.04 kg/hr DCH bottom rate). DCH recovery is calculated to be 96.3 percent (1.05 kg/hr÷1.09 kg/hr×100).

As can be seen from the foregoing, Example 1 according to the present invention is capable of obtaining a recovery of DCH greater than that obtained according to the Comparative Example without imposing a high vacuum condition on the distillation column.

Advantages of the present invention include:
1. A wider selection of vacuum devices and the ability to use of a more economical steam-jet ejector, thereby reducing capital and operating costs;
2. Reduction of column size for a given feed volume due to the ability to operate at higher pressures, further reducing capital investment required;
3. Reduced heavy byproducts formation due to reduced distillation bottoms temperatures for increased product yield and reduced energy requirements for byproduct disposal;
4. Additional water introduced by steam stripping facilitates any downstream epoxidation process by keeping the concentration of sodium chloride formed during epoxidation below the saturation level.

What is claimed is:
1. A process for recovering dichlorohydrin(s) from a mixture comprising dichlorohydrin(s); one or more compounds selected from the group consisting of chlorohydrins, ester(s) of chlorohydrin(s), monochlorohydrin(s), ester(s) of monochlorohydrin(s), ester(s) of dichlorohydrin(s), multihydroxylated-aliphatic hydrocarbon compound(s) and ester(s) of multi hydroxylated-aliphatic hydrocarbon compound(s); water; and optionally one or more substances comprising chlorinating agent(s), catalyst(s), ester(s) of catalyst(s), or heavy byproduct(s), wherein the process comprises:

(a) providing a vapor and/or liquid phase mixture obtained from a hydrochlorination reaction comprising dichlorohydrin(s); one or more compounds selected from the group consisting of chlorohydrins, ester(s) of chlorohydrin(s), monochlorohydrin(s), ester(s) of monochlorohydrin(s), ester(s) of dichlorohydrin(s), multihydroxylated-aliphatic hydrocarbon compound(s) and ester(s) of multihydroxylated-aliphatic hydrocarbon compound(s); water, wherein the water present in the mixture is the water produced in the hydrochlorination reaction; and optionally one or more substances comprising chlorinating agent(s), catalyst(s), ester(s) of catalyst(s), or heavy byproduct(s);

(b) distilling or fractionating the mixture of step (a) in at least a first separation unit operation to separate a lower boiling fraction comprising dichlorohydrin(s) and other lower boiling components from the mixture of step (a), to form a higher boiling fraction comprising the residue of the distillation or fractionation; wherein step (b) comprises:

(b1) vaporizing an azeotropic mixture of dichlorohydrin(s) and water from the mixture of step (a) to separate a lower boiling fraction comprising at least dichlorohydrin(s) and water from the mixture of step (a); and (b2) condensing the low boiling fraction of step (b1) to form a liquid aqueous phase and a liquid organic phase comprising dichlorohydrin(s); or (ii) wherein step (b) further comprises:

(b3) separating the liquid aqueous phase of step (b2) from the liquid organic phase of step (b2); and (b4) recycling at least some of the liquid aqueous phase of step (b3) to step (b1) and/or step (b2);

(c) transferring the higher boiling fraction from step (b) to at least a second separation unit operation; and introducing a stripping agent into the higher boiling fraction in the at least second separation unit operation; wherein the stripping agent is an azeotroping agent for the dichlorohydrin(s); and wherein the stripping agent contacts the higher boiling fraction and strips dichlorohydrin(s) from the higher boiling fraction into a vapor phase; wherein a vapor fraction comprising dichlorohydrin(s) and stripping agent is produced in the at least second separation unit operation; and wherein the formation of heavy byproducts is minimized;

(d) recovering at least a portion of the lower boiling fraction of step (b) and the vapor fraction of step (c); and (e) combining the lower boiling fraction produced in step (b) with the vapor fraction produced in step (c).

2. The process of claim 1, (i) wherein at least one chlorinating agent is present in the mixture provided in step (a); and wherein the at least one chlorinating agent comprises hydrogen chloride; or (ii) wherein at least 50 percent of the chlorinating agent(s) present in the mixture provided in step (a) is removed from the mixture provided in step (a) prior to step (c); and wherein 10 to 95 percent of the total amount of dichlorohydrin(s) in the mixture provided in step (a) is recovered in the lower boiling fraction of step (b).

3. The process according to claim 1, wherein step (b) is carried out at a pressure in the range from 1 kPa to 0.12 MPa; and wherein the temperature of the higher boiling fraction during step (b) is in the range from 50° C. to 139° C.

4. The process according to claim 1, wherein the stripping agent comprises steam.

5. The process according to claim 1, wherein at least one monochlorohydrin or ester of at least one monochlorohydrin(s) is present in the mixture provided in step (a) and in the high-boiling fraction of step (b); or wherein at least one multihydroxylated-aliphatic hydrocarbon compound or ester of at least one multihydroxylated-aliphatic hydrocarbon compound is present in the mixture provided in step (a) and in the high-boiling fraction of step (b).

6. The process according to claim 1, (1) wherein the mixture provided in step (a) further comprises a catalyst for hydrochlorinating monochlorohydrin(s), ester(s) of monochlorohydrin(s), multihydroxylated-aliphatic hydrocarbon compound(s), or ester(s) of multihydroxylated-aliphatic hydrocarbon compound(s); and wherein the catalyst is at least one carboxylic acid, at least one ester of at least one carboxylic acid, or a combination thereof, having a boiling point during step (b) greater than the boiling point of the highest boiling dichlorohydrin during step (b); (2) wherein the catalyst (i) is a carboxylate derivative having from two to about 20 carbon atoms and containing at least one functional group selected from the group comprising an amine, an alcohol, a halogen, a sulfhydryl, an ether, an ester, or a combination thereof, wherein the functional group is attached no closer to the acid function than the alpha carbon; or a precursor thereto; (ii) is less volatile than the dichlorohydrin(s); and (iii) contains heteroatom substituents.

7. The process according to claim 1, wherein byproducts are present in the mixture provided in step (a); and wherein the amount of heavy byproducts in the high boiling fraction of step (b) does not exceed 110 percent of the amount of heavy byproducts in the mixture provided in step (a).

8. The process according to claim 1, or claim 7, (i) wherein dichlorohydrin(s) are recovered from the lower boiling fraction of step (b) and/or the vapor fraction of step (d); or (ii) wherein the lower boiling fraction and vapor fraction recovered in step (d) are subjected to epoxidation to form epichlorohydrin without additional purification of the dichlorohydrin(s) other than optionally via distillation or fractionation according to claim 7.

9. The process according to claim 1, (i) wherein all of the steps of the process are carried out simultaneously with each other and the process is carried out continuously; or (ii) wherein at least a portion of the higher boiling fraction treated in step (c) is recycled to the hydrochlorination step; or (iii) wherein at least 95 percent of the dichlorohydrin(s) produced during hydrochlorination is recovered in step (d).

10. The process according to claim 1, wherein combining step (e) is carried out after distilling or fractionating the vapor fraction of step (c) for isolating dichlorohydrin(s) and stripping agent.

11. The process according to claim 1, wherein combining step (e) is carried out before distilling or fractionating the vapor fraction of step (c).

* * * * *